United States Patent [19]

Daniel et al.

[11] Patent Number: 5,425,731
[45] Date of Patent: Jun. 20, 1995

[54] INSTRUMENT FOR CUTTING, COAGULATING AND ABLATING TISSUE

[75] Inventors: Steven A. Daniel, Fremont; Mark J. Cowell, San Carlos, both of Calif.

[73] Assignee: Metcal, Inc., Menlo Park, Calif.

[21] Appl. No.: 32,160

[22] Filed: Mar. 12, 1993

Related U.S. Application Data

[63] Continuation of Ser. No. 680,859, Apr. 5, 1991, abandoned.

[51] Int. Cl.$^6$ ............................................. A61B 17/36
[52] U.S. Cl. ..................................... 606/28; 219/229; 606/29; 606/32
[58] Field of Search ............... 606/24, 28, 33, 45, 606/29, 30, 31; 219/229; 128/399, 401, 402

[56] References Cited

U.S. PATENT DOCUMENTS

| | | | |
|---|---|---|---|
| 3,653,385 | 4/1972 | Burton | 606/27 |
| 4,185,632 | 1/1980 | Shaw | 219/233 X |
| 4,745,264 | 5/1988 | Carter | 219/229 X |
| 4,752,673 | 6/1988 | Krumme | 219/229 X |
| 4,794,226 | 12/1988 | Derbyshire | 219/553 X |
| 4,832,979 | 5/1989 | Hoshino | 606/28 |
| 4,877,944 | 10/1989 | Cowell et al. | 219/548 |
| 4,877,944 | 10/1989 | Cowell | 219/548 |
| 5,087,256 | 2/1992 | Taylor et al. | 606/28 |

*Primary Examiner*—Peter A. Aschenbrenner
*Attorney, Agent, or Firm*—Howard L. Rose

[57] ABSTRACT

An instrument for cutting, ablating and coagulating tissue has a rod of ferromagnetic material fusion welded to the base of a conical tip of copper with the rod adjacent the base of the conic being of lesser diameter than the base to provide a region to accept a potted coil of wire about the rod whereby when the coil is connected to a constant current high frequency source the rod and tip are heated to a temperature approaching the Curie temperature of the ferromagnetic rod. As Curie temperature is approached the rod becomes essentially non-magnetic heating decreases to produce a temperature below Curie temperature and the cycle repeats. As a result of the excellent heat exchange interfaces produced by fusion welding the energy delivered to the tissue or other load which may be non-biological is closely controlled by temperature which is self regulated. A ferromagnetic sleeve is placed about the coil to concentrate magnetic flux in the rod. An outer sleeve spaced radially from the ferromagnetic sleeve and of relatively non-heat conductive material extends from the base of the tip away from the tip to provide a handle for the instrument.

15 Claims, 1 Drawing Sheet

INSTRUMENT FOR CUTTING, COAGULATING AND ABLATING TISSUE

This is a continuation of application Ser. No. 07/680,859, filed on Apr. 5, 1991 now abandoned.

The present invention relates to an instrument for cutting, coagulating and ablating human and animal tissue and more particularly a temperature self regulating surgical instrument of simple design and high efficiency.

BACKGROUND OF THE INVENTION

Currently there are a number of instruments for effecting the same general results as the device of the present invention.

Contact lasers generate heat at a tip of a quite short optical fiber which is brought into contact with tissue to be treated. These devices produce high tissue damage, are expensive and produce poor coagulation.

Non-contact lasers located external to the body direct energy produced by a laser through an elongated optical fiber to the tissue. These devices suffer from all of the same faults as the contact lasers and in addition provide poor tactile feedback.

Hot scalpels comprise a heated blade to provide easier cutting than conventional scalpels and produce some coagulation during cutting. Again there is high tissue damage and the cutting edge dulls quickly. As such, the device is increasingly in limited use.

Ultrasonic scalpels are the product of an emerging technology about which little is known at the moment. This scalpel employs a cutting blade that is vibrated at ultrasonic frequencies which in practice is stated to enhance cutting and coagulation of tissue.

In electro-cautery, an electrical potential is developed at the end of the device to produce an arc at the end. The arc is used to cut, ablate and coagulate electrically grounded tissue. The device produces high tissue damage at the site of the arc, also the tissue must be grounded and this is accomplished through body fluids thus having the potential for tissue damage at unknown locations.

BRIEF DESCRIPTION OF THE PRESENT INVENTION

The device of the invention comprises a cylindrical ferromagnetic member or rod having a tip of desired shape and highly heat conductive material secured to one end of the cylindrical member, a coil of wire wound about the cylindrical member and adapted to be connected to a source of constant high frequency current, the coil being potted in a thermally conductive material to maximize heat transfer to the tip but is thermally insulated by space from a cylindrical sidewall of the apparatus to reduce heat applied to tissue not to be heated.

The Curie temperature of the ferromagnetic material is chosen to temperature self regulate at an appropriate point but the important feature of the present invention is that the amount of energy delivered to the tissue is relatively precisely controlled. Specifically temperature cannot do work. It is the energy delivered that does the work. Thus there must be very tight coupling between the tip and the ferromagnetic member so that energy and temperature are closely related. This feature is accomplished by welding the tip to the ferromagnetic rod preferably by fusion welding, the latter providing excellent thermal communication between tip and rod whereby the energy delivered is managed directly and tissue damage is greatly reduced relative to other available devices.

As is explained in U.S. Pat. No. 4,256,945, the current supplied in such a system must be constant. If current is held constant then the equation $P = I^2 R$ becomes $P = KR$, where K is a constant equal to $I^2$. Under these conditions below Curie temperature current is confined by skin effect to a narrow region of the ferromagnetic rod and the factor R is high. When the temperature of the rod approaches effective Curie temperature the permeability of the rod is greatly reduced, the current spreads more evenly through the rod and the resistance is greatly reduced. The heating factor is greatly reduced and the temperature of the rod falls below Curie temperature and the cycle repeats.

The term "constant current" as used herein is defined by the equation $$\frac{\Delta |I|}{|I|} \leq -1/2 \frac{\Delta |R|}{|R|}$$

As long as this equation is observed temperature regulation is achieved; the control being tighter the greater the disparity between the two sides of the equation or more particularly, the more rigid the current control the more constant the temperature.

The term "effective Curie temperature" as used herein refers to the fact that at temperatures of from 1° C. to 100° C. below absolute Curie temperature a ferromagnetic material may achieve a permeability reduced sufficiently to produce temperature regulation.

The term "ferromagnetic material" as used herein refers to iron-nickel alloys, other iron alloys, such as Series 400 stainless steel, ferrites and the like which change magnetic permeability as a function of temperature.

OBJECTS OF THE INVENTION

It is an object of the present invention to provide a surgical instrument for cutting, coagulating and ablating tissue which is simple of construction.

It is another object of the present invention to provide a hot tip scalpel providing carefully controlled delivery of energy to tissue to be treated.

Yet another object of the present invention is to provide a heated surgical instrument that has a cutting surface of uniform temperature throughout.

Still another object of the invention is to provide a heated ferromagnetic member fusion welded to a highly heat conductive tip with the ferromagnetic member heated by induction heating to a temperature in the range of its Curie temperature whereby the instrument is self regulating.

The above and other features, objects and advantages of the present invention, together with the best means contemplated by the inventors thereof for carrying out their invention will become more apparent from reading the following description of a preferred embodiment and perusing the associated drawing in which:

BRIEF DESCRIPTION OF THE DRAWING

The drawing is a side view in section of the instrument of the present invention.

DETAILED DESCRIPTION OF THE INVENTION

Figure 1:
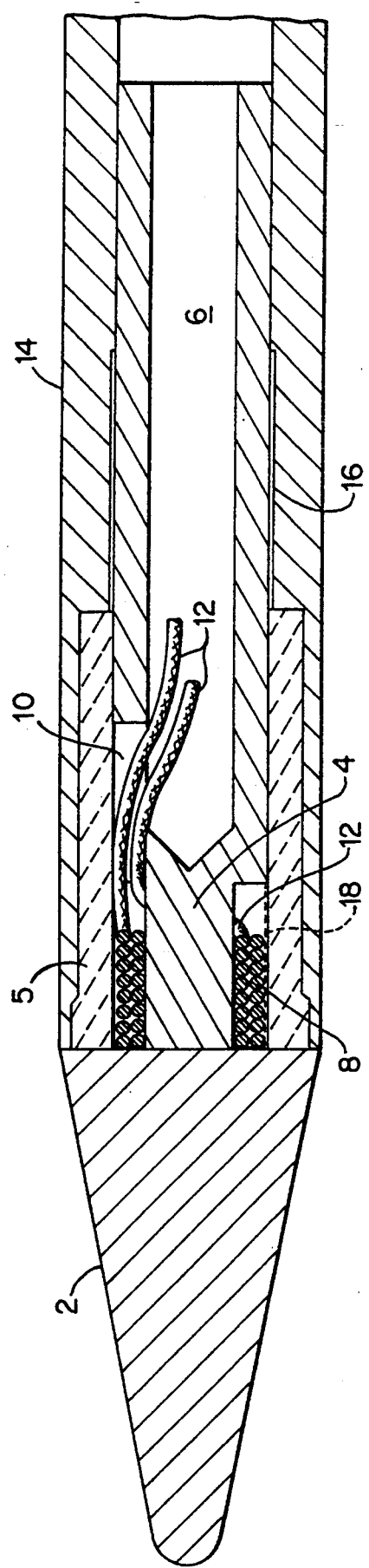

Referring now specifically to the single FIGURE of the drawing, there is provided a tip 2, preferably conical, of a highly heat conductive material such as copper. Attached to the base of the conical tip is a rod 4 of ferromagnetic material which has been axially drilled from right to left as viewed in the drawing to provide a channel 6 to within a prescribed distance of the tip.

A coil of wire 8 is wound about the rod 4 adjacent the base of the tip 2. The rod 4 has a side opening 10 to accept wires 12 from the coil which extend through channel 6 to an external source of constant current, not illustrated. The rod 4 and coil 8 are dimensioned such as to be roughly three-fourths the diameter of the base of the tip 2. The coil is preferably potted in a suitable material such as a 50/50 mixture of electrically non-conductive, heat conductive TGC-120 borosilica glass and Type 1500 crossover paste.

An outer sleeve 14 of non-magnetic stainless steel, Series 300, for instance, has an outer diameter about equal to the base of the tip 2 and extends therefrom a distance suitable to provide a handle for the scalpel. The sleeve is supported at the base of the tip and towards the right end, as viewed in the drawing, by the rod 4. A small annular clearance at 16 is provided over about half the length of overlap of the rod 4 and sleeve 14 which in conjunction with the gap between the coil 8 and sleeve 14 and the fact the Stainless 300 is a poor conductor of heat maintains the right part of the sleeve 14 at a temperature such as to be comfortable to hold.

The coil may have a sleeve of ferromagnetic material, a sleeve 18, overlying it to reduce spread of the magnetic field and help confine the field to the rod 4.

The coil of wire 4 may be replaced with a coated coil. Specifically a thin layer of non-conductive material may be dispersed over the rod where the coil 4 is located in the drawing. A helix of conductive material may now be formed on top of the insulative coating in one or more mutually insulated layers to provide the required magnetic flux.

In the manufacture of the device as presently contemplated a rod of copper and a rod of stainless steel selected from the 400 series, the rods being of equal diameters of about one-eighth inch, are fusion-welded end to end. The rod 4 is then machined down to desired size, about half the diameter or slightly less than the diameter of the base of the tip 2. The tip is also machined to desired shape, in the embodiment illustrated, a rounded end conic.

In the machining operation, a layer of ferromagnetic material is preferably, though not necessarily, left on the base of the tip 2. Such layer further reduces the spread of the magnetic field.

It is preferred to employ fusion welding, sometimes referred to as inertial welding, since such a procedure permits welding of otherwise incompatible materials. Further this procedure provides an excellent heat transfer bond so that the temperature of the tip closely follows the temperature of the rod and thus transfer of energy to the tissue to be treated is carefully controlled.

The constant current may be supplied by constant current supplies such as disclosed in U.S. Pat. Nos. 4,626,767 and 4,752,864 assigned to the same assignee as the present invention. Similar results can be achieved by the use of supplies such as disclosed in U.S. Pat. Nos. 4,769,519 and 4,795,886 also assigned to the same assignee of the present invention.

In use the scalpel is used in the conventional manner of heated blade or laser scalpels being moved over the tissue to be cut, removed or otherwise treated. The temperature of the tip and rod are carefully controlled so that energy delivered does not exceed desired levels and product excessive tissue damage.

It should be noted that the use of a copper tip or tip of some other highly heat conductive material, insures a uniform temperature throughout the tip so that the instrument may be used in any position convenient to the surgeon.

Once given the above disclosure, many other features, modifications and improvements will become apparent to the skilled artisan. Such features, modifications and improvements are, therefore, considered to be a part of this invention, the scope of which is to be determined by the following claims.

We claim:

1. An instrument for cutting, coagulating and ablating tissue comprising:
    a tapered tip of highly heat conductive material having a base,
    a rod of ferromagnetic material secured to the base of said tapered tip by means of a highly heat conductive junction,
    said rod being of lesser diameter than the base of said tapered tip providing an exposed region of said base,
    a thin layer of ferromagnetic material disposed along the exposed region of said base, and
    a coil of wire wound about said rod adjacent the base of said tip;
    said coil of wire when energized by a constant alternating current inducing a magnetic field in said rod to heat it sufficiently to cause said member to approach its Curie temperature sufficiently to reduce its magnetic permeability.

2. An instrument according to claim 1 further comprising
    a ferromagnetic sleeve disposed over said inductor.

3. An instrument according to claim 2 wherein
    said inductor is a helix of conductive material disposed about said rod adjacent said tip.

4. An instrument according to claim 2 wherein
    said helix is a coil of wire, and
    wherein a ferromagnetic sleeve is disposed closely about said coil of wire.

5. An instrument according to claim 2 further comprising
    a sleeve of non-magnetic, poor heat conductive material disposed about and spaced radially from said rod.

6. An instrument according to claim 5 wherein
    said inductor is potted in a poor electrically conductive, highly heat conductive material.

7. An instrument for cutting, ablating and coagulating tissue comprising
    a tip of highly heat conductive material having a generally circular base,
    a rod of ferromagnetic material of lesser diameter than the base of said tip fusion welded centrally of the base of said tip,
    a coil of wire wound about said rod adjacent the base of said tip, said coil of wire being potted in an electrically non-conductive, highly heat conductive potting material, and a non-magnetic, poor heat conductive sleeve disposed about said rod, said sleeve being of essentially the same diameter as the base of said tip and extending from the base of said tip away therefrom and enveloping and spaced radially from said rod adjacent said tip.

8. An instrument according to claim 7 wherein said rod has a region remote from said tip having an outer diameter equal to the inner diameter of an adjacent region of said sleeve.

9. An instrument according to claim 7 further comprising a ferromagnetic sleeve surrounding said coil and in contact with turns of said coil and said potting material.

10. An instrument according to claim 7 and claim 9 wherein the portion of the base of said tip that is not covered by said rod is covered by a thin layer of ferromagnetic material.

11. The method of making an instrument for cutting, ablating and coagulation matter comprising the steps of securing a first rod of highly heat conductive material to a second rod of ferromagnetic material, shaping the first rod to provide a tip with a base, reducing the diameter of a region of the second rod adjacent the first rod relative to said first rod to provide an exposed area of base of the first rod, winding a coil of wire about at least a part of the region of reduced diameter of the second rod adjacent the first rod, and potting the coil of wire in an electrically non-conductive, highly heat conductive material.

12. The method of making an instrument according to claim 11 further comprising the step of placing a ferromagnetic sleeve over the coil before the potting material has set to bind the sleeve to the coil and potting material.

13. The method of making an instrument according to claim 12 further comprising reducing the diameter of the region of the second rod such as to leave a thin layer of ferromagnetic material on the base of the tip exposed by reducing the diameter of the second rod.

14. The method of making an instrument according to claim 12 further comprising the step of placing a relatively non-heat conductive sleeve of a diameter about equal to the outer diameter of the base of the first rod about and spaced radially outward from the second rod.

15. The method of making an instrument according to claim 14 wherein the step of reducing the diameter of said second rod reduces the diameter sufficiently that an air gap is established between the first mentioned sleeve and the inner diameter of the non-heat conductive sleeve.

* * * * *